United States Patent

Evans

(10) Patent No.: US 8,795,800 B2
(45) Date of Patent: Aug. 5, 2014

(54) WATER RESISTANT MEDICAL BANDAGING PRODUCT

(75) Inventor: John C. Evans, Lancashire (GB)

(73) Assignee: BSN Medical, Inc., Charlotte, NC (US)

( * ) Notice: Subject to any disclaimer, the term of this patent is extended or adjusted under 35 U.S.C. 154(b) by 653 days.

(21) Appl. No.: 13/044,843

(22) Filed: Mar. 10, 2011

(65) Prior Publication Data

US 2011/0244748 A1 Oct. 6, 2011

Related U.S. Application Data

(60) Provisional application No. 61/312,425, filed on Mar. 10, 2010.

(51) Int. Cl.
*D04H 1/00* (2006.01)
*D04B 21/16* (2006.01)
*A61F 13/04* (2006.01)
*D04B 1/16* (2006.01)
*A61F 13/00* (2006.01)

(52) U.S. Cl.
CPC ..... *A61F 13/041* (2013.01); *A61F 2013/00889* (2013.01); *A61F 2013/00097* (2013.01); *A61F 2013/00251* (2013.01); *A61F 2013/00859* (2013.01); *D04B 21/16* (2013.01); *A61F 2013/00395* (2013.01); *D10B 2509/028* (2013.01); *A61F 2013/00238* (2013.01); *D04B 1/16* (2013.01)

USPC .......................... 428/36.1; 442/304; 442/305

(58) Field of Classification Search
CPC ................ A61F 13/00; A61F 13/0008; A61F 13/00004; D10B 2509/02; D10B 2509/022; D10B 2509/028; D04B 11/00; D04B 1/00; D04B 1/14; D04B 1/16
USPC .................................. 442/304, 305; 428/36.1
See application file for complete search history.

(56) References Cited

U.S. PATENT DOCUMENTS

| 3,504,672 | A | * | 4/1970 | Moon | 602/75 |
| 6,000,366 | A | | 12/1999 | Reeping | |
| 6,159,877 | A | | 12/2000 | Scholz et al. | |
| 6,555,730 | B1 | * | 4/2003 | Albrod et al. | 602/58 |
| 2002/0115369 | A1 | * | 8/2002 | Yokoyama et al. | 442/308 |
| 2008/0287852 | A1 | * | 11/2008 | Evans | 602/43 |
| 2009/0208699 | A1 | | 8/2009 | Miyauchi et al. | |

OTHER PUBLICATIONS

International Search Report for PCT/US2011/027867 dated May 3, 2011.

\* cited by examiner

*Primary Examiner* — Elizabeth Cole
(74) *Attorney, Agent, or Firm* — Shumaker, Loop & Kendrick, LLP

(57) ABSTRACT

A water resistant article for positioning on an appendage to be treated comprises a knitted body constructed from synthetic yarns is provided, wherein each of the synthetic yarns comprise a bundle of substantially parallel fine monofilaments.

5 Claims, 10 Drawing Sheets

WATER RESISTANT MEDICAL BANDAGING PRODUCT

This application claims priority to U.S. Provisional Application No. 61/312,425, which is hereby incorporated by reference in its entirety herein.

TECHNICAL FIELD AND SUMMARY OF THE INVENTION

The present invention relates generally to the field of medical bandaging products, and more particularly, to a water resistant orthopedic device constructed of synthetic monofilament yarn for use in casting, splinting, padding or general protection of the anatomy.

Traditionally, cotton stockinettes and bandages have been used to protect and cushion the skin and boney prominences prior to the application of a cast or splint. Materials conventionally used in these types of medical products include both natural and synthetic materials. While natural materials such as cotton typically provide greater comfort than synthetic materials, natural materials are prone to moisture absorption and are extremely difficult to dry out if they become wet. Thus, great care must be taken by the patient to keep the material dry during daily activities, such as showering. In contrast, while synthetic materials are more resistant to water absorption, they are typically less comfortable to the patient and thus are not typically used as undercast paddings.

Accordingly, it would be desirable to provide a medical bandaging product for use as an undercast padding or other application that includes both the comfort provided by natural materials and the water resistant properties of synthetic materials.

To overcome the disadvantages of prior art medical bandaging products described above, in one aspect a medical bandaging product is provided herein constructed from multiple threads made up of a plurality of fine, generally parallel arranged monofilaments to provide a soft texture and resistance to moisture absorption.

In another aspect, a water resistant breathable fabric formed or knitted into a circular tube is provided that fits comfortably over an injured limp or extremity of the anatomy.

In yet another aspect, the fabric is knitted to provide a flat or 3D geometry.

In yet another aspect, the construction of the medical bandaging product renders the fabric very open, allowing the underlying skin to breathe effectively during wear.

In yet another aspect, the fabric numbers about 342 openings/in$^2$ (53 openings/cm$^2$) a relaxed form.

In yet another aspect, the fabric is devoid of elastic threads to improve conformability, but has an 'elastic tendency' created by the knitted structure, which allows the bandage to fit snuggly over the limb/anatomy.

In yet another aspect, the thread type allows water to escape and drain away very effectively through the cast or splint, thereby allowing the skin to breathe and dry naturally.

In yet another aspect, the medical bandaging product is devoid of chemical finishes to render the fabric water resistant, thus eliminating sensitization issues of the skin.

In yet another aspect, the monofilaments are uncoated synthetic fibers.

In yet another aspect, the monofilaments are nylon or nylon 66.

In yet another aspect, the monofilaments are polypropylene.

In yet another aspect, the filaments are substantially parallel and number between about 10 and about 20 such that the fabric is flexible and soft to the touch.

In yet another aspect, the fabric has a mass per unit area of about 20 g/m$^2$ or greater, and may preferably range between 20 g/m$^2$ to 120 g/m$^2$.

Additional features and advantages of the invention will be set forth in the detailed description which follows, and in part will be readily apparent to those skilled in the art from that description or recognized by practicing the invention as described herein.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1:
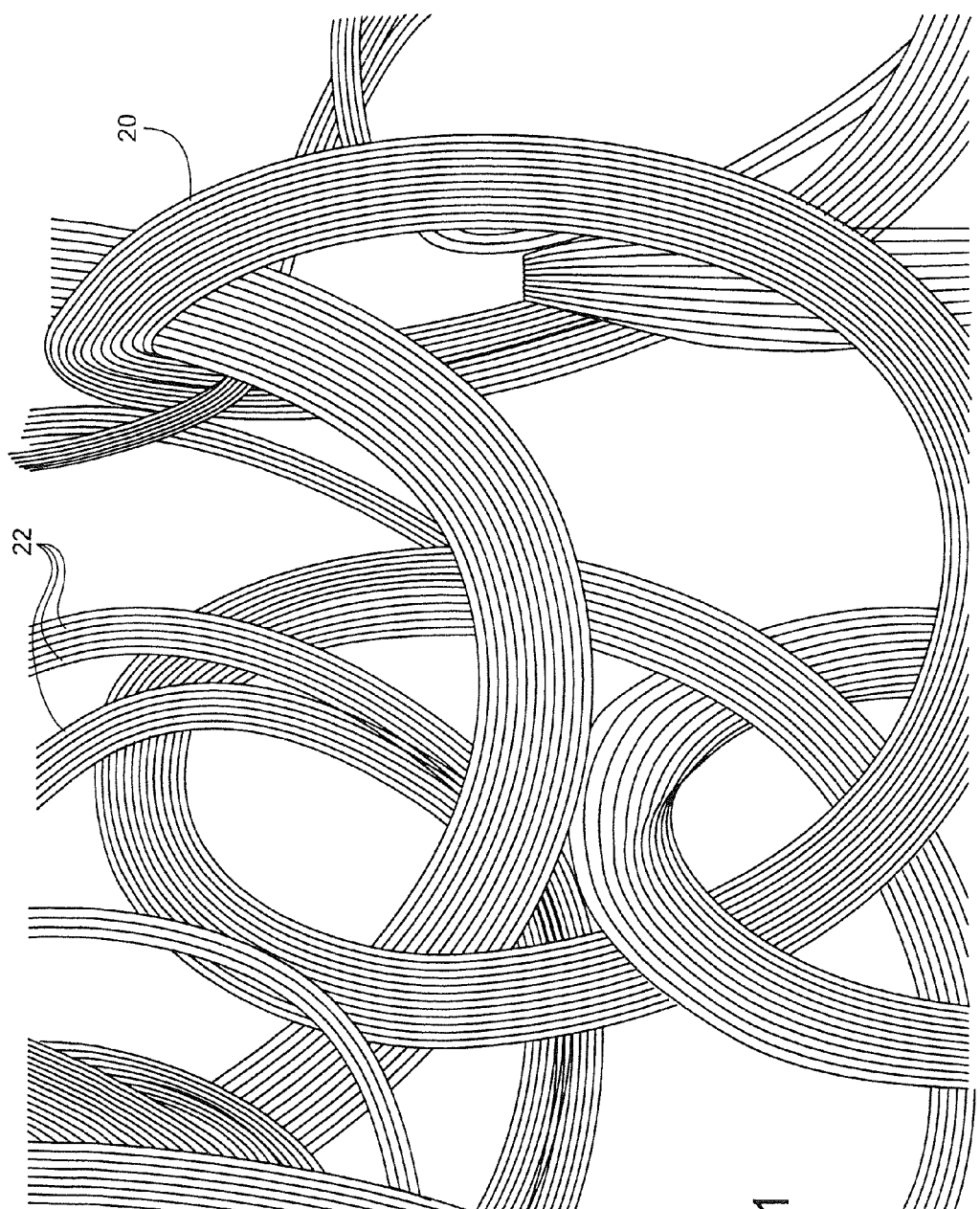
FIGS. 1-7 are various magnified views of portions of the fabric in accordance with an embodiment of the invention.
Figure 2:
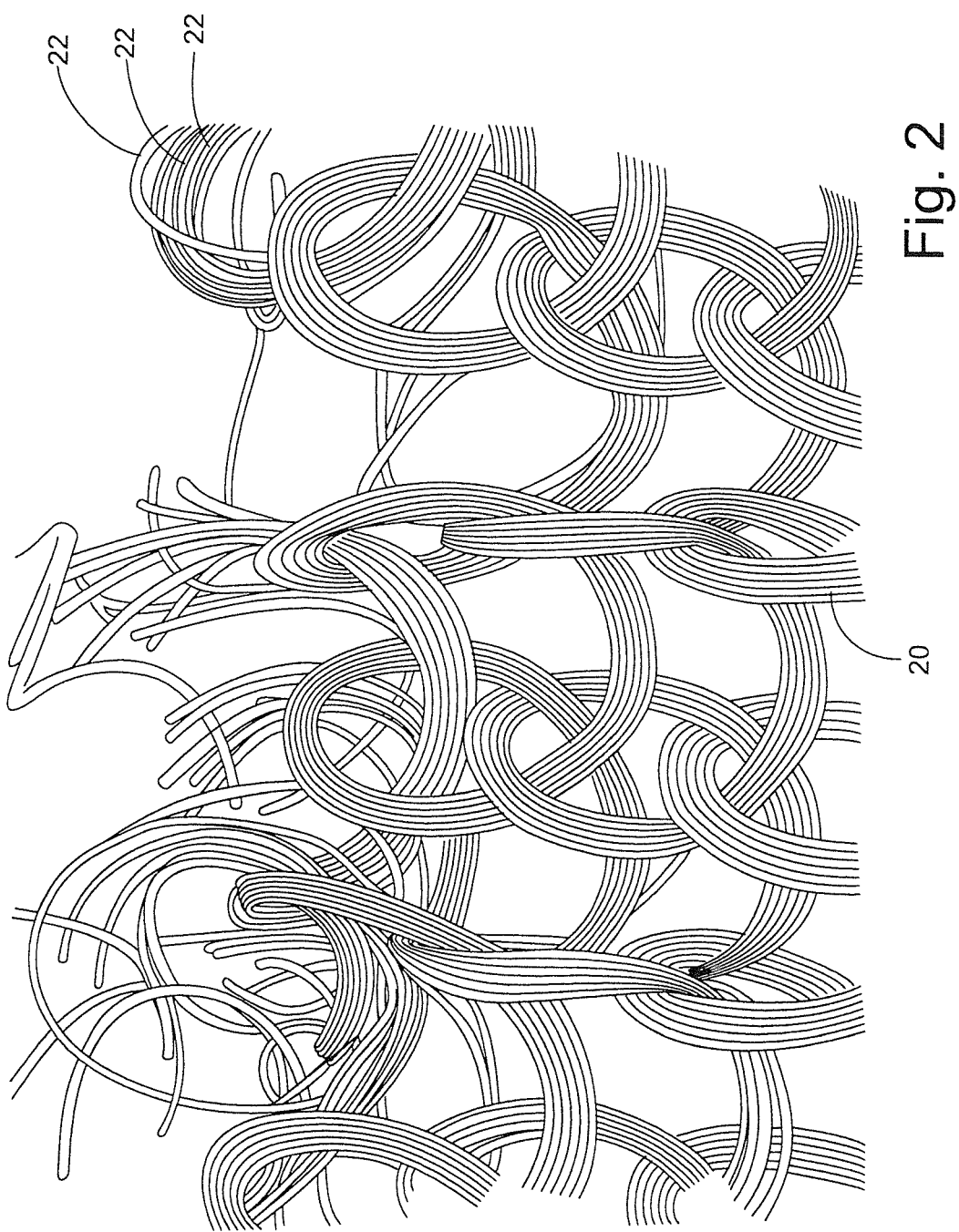
Figure 3:
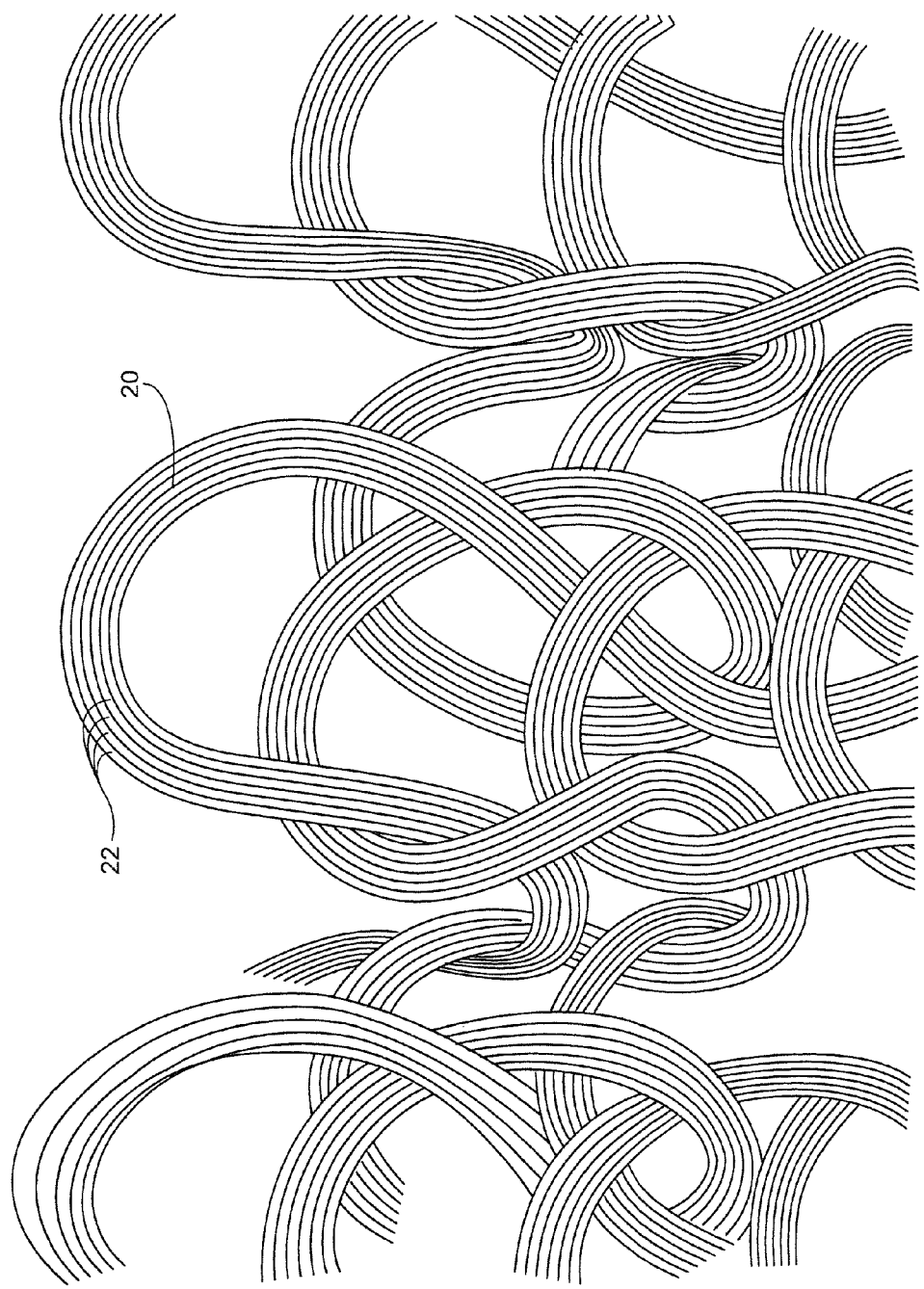
Figure 4:
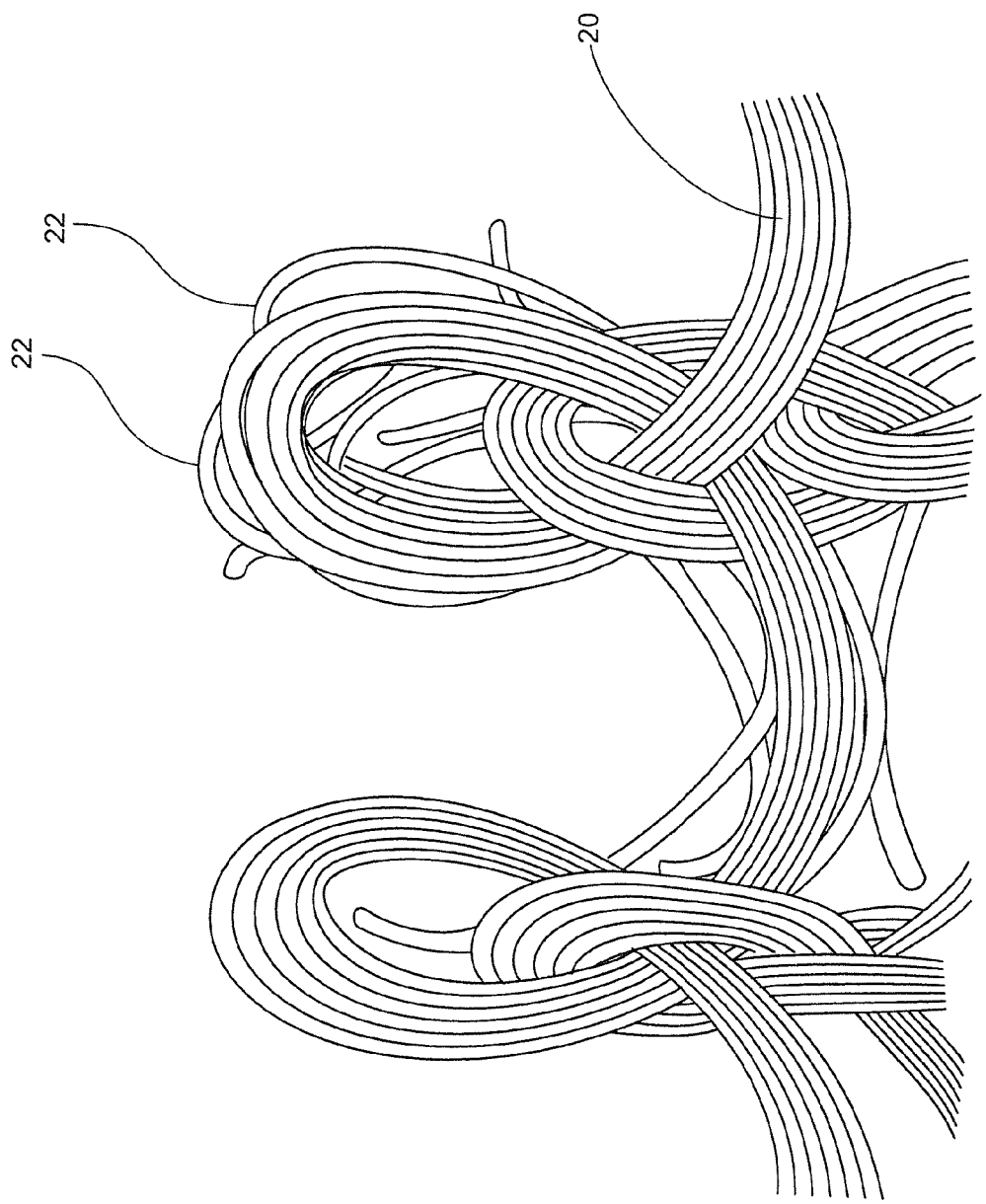
Figure 5:
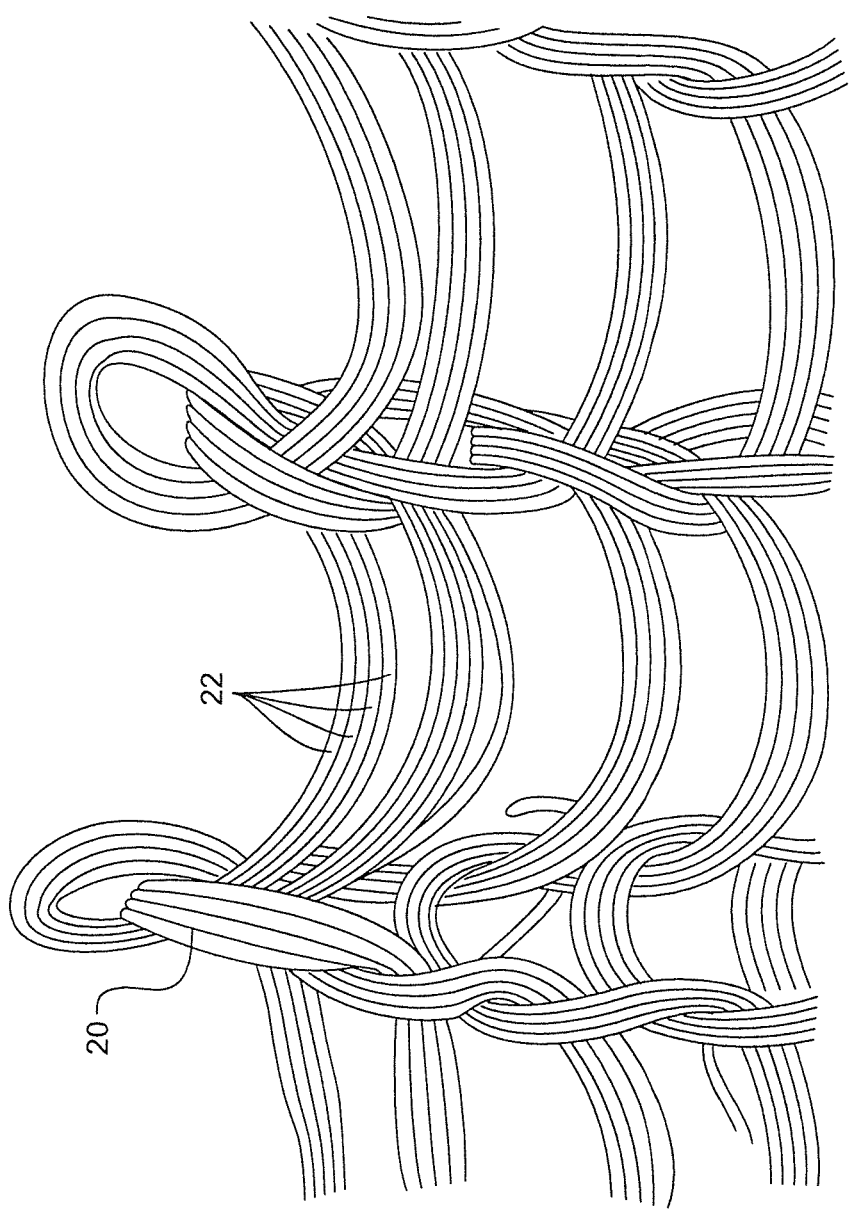
Figure 6:
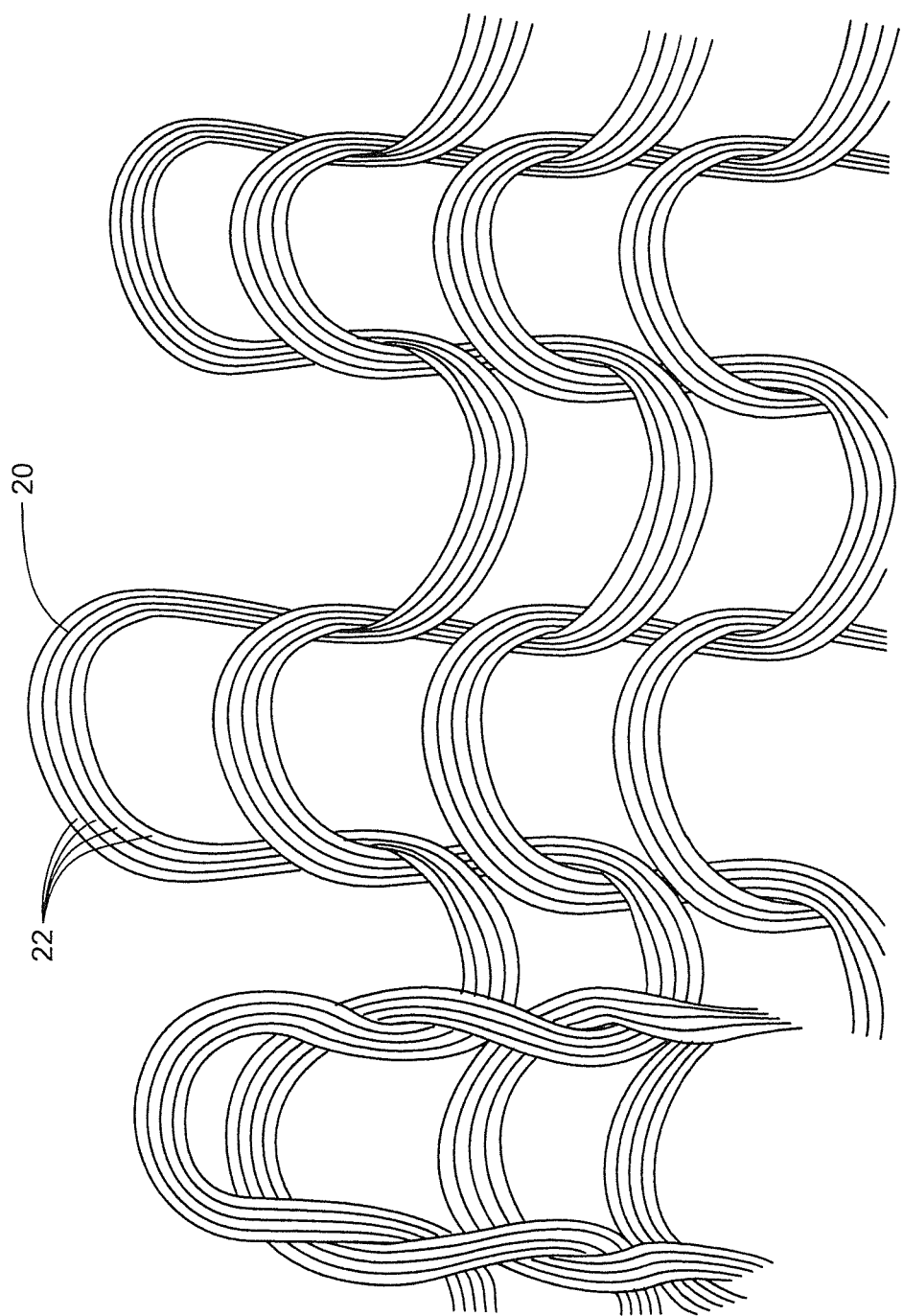
Figure 7:
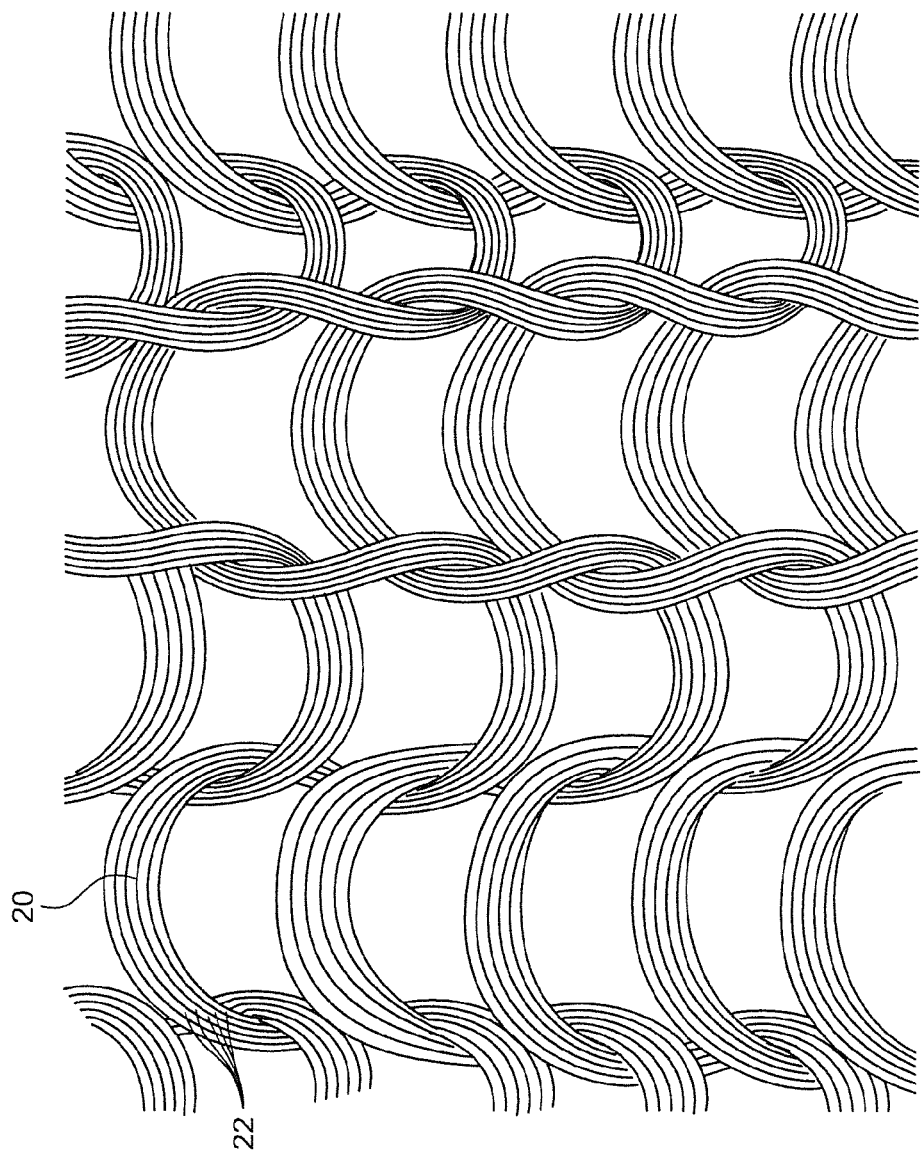

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention.

Referring now FIGS. 1-7, magnified images of a knitted fabric 20 constructed from bundles of fine monofilament threads 22 are shown. Each yarn of the fabric includes multiple fine monofilaments, arranged generally parallel into bundles, to provide a soft texture and a structure that does not unduly ladder or fray. The use of multiple monofilament yarns significantly increases the surface area of the fabric and reduces surface tension, which allows fluids and vapors to pass rapidly through the fabric and allow bandages and sleeves formed therefrom to dry very quickly upon exposure to moisture. This is a distinct and significant advantage over the common practice of using relatively large yarns.

In normal circumstances, monofilaments of the type used in the present invention would be hard and inflexible and would therefore be uncomfortable against the skin. This issue is overcome in the present invention by the use of a single thread split into multi-threads of fine monofilaments. In an exemplary embodiment, the rather voluminous bundle of nearly parallel filaments numbers is between about 10 and about 20 monofilaments to provide the desired flexibility and "softness" of the fabric.

One suitable example of synthetic monofilament includes, but is not limited to nylon or nylon 66 monofilament. Other synthetic yarns, for example, polypropylene, may be provided in bundled groups to achieve the same or similar result. The porosity of the fabric is structured to rapidly dry and allow the skin to breathe, and in one specific embodiment, the fabric structure has a mass per unit area of about 20 g/m$^2$, and may preferably range between 20 g/m² to 120 g/m². The "openness" of the fabric allows the skin to breathe effectively during wear, and in one specific embodiment, the fabric structure results in about 342 openings/in² (53 openings/cm²) (in a relaxed form).

The fabric may be knitted on a circular knitting machine, also referred to as a "weft knitting machine," to provide a sleeve geometry to be placed over a limb. The fabric may also be knitted on a warp knitting machine in the form of a flat or 3D geometry fabric, which may be wrapped of the limp. The knitting construction may be produced on a single dial and cylinder or on a double needle bed machine.

The use of multiple threads of fine monofilament obviates the need for chemical finishes for water resistance, thus eliminating skin sensitization issues. The use of multiple threads of fine monofilament also obviates the need for incorporating elastic threads into the fabric to improve conformability, as an elastic tendency is inherently created by the knitted structure and use of the fine monofilament which allows the fabric to conform to the underlying anatomy.

Figure 8:
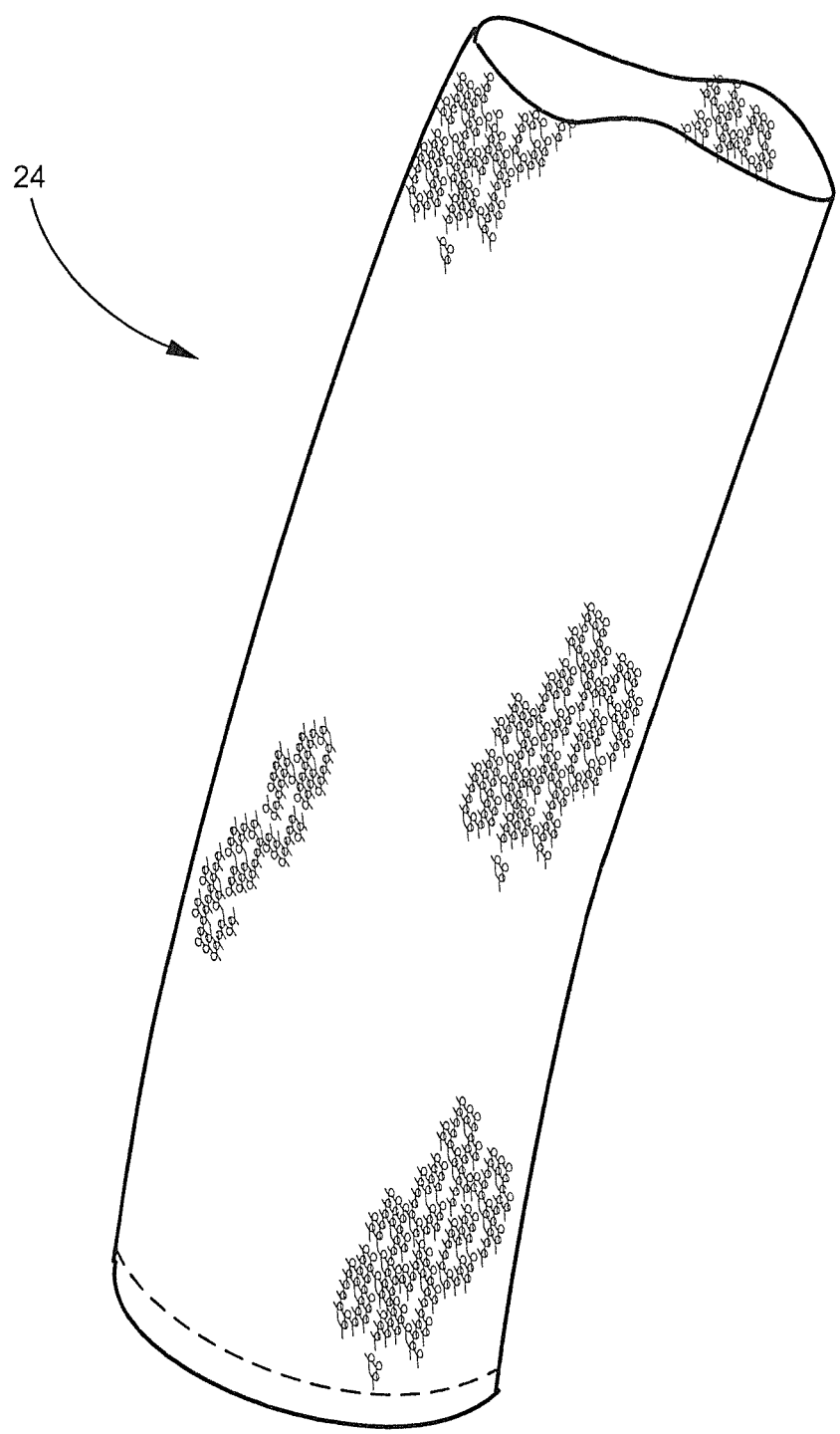
FIG. 8 is a perspective view of a tubular stockinette form of the invention.
Figure 9:
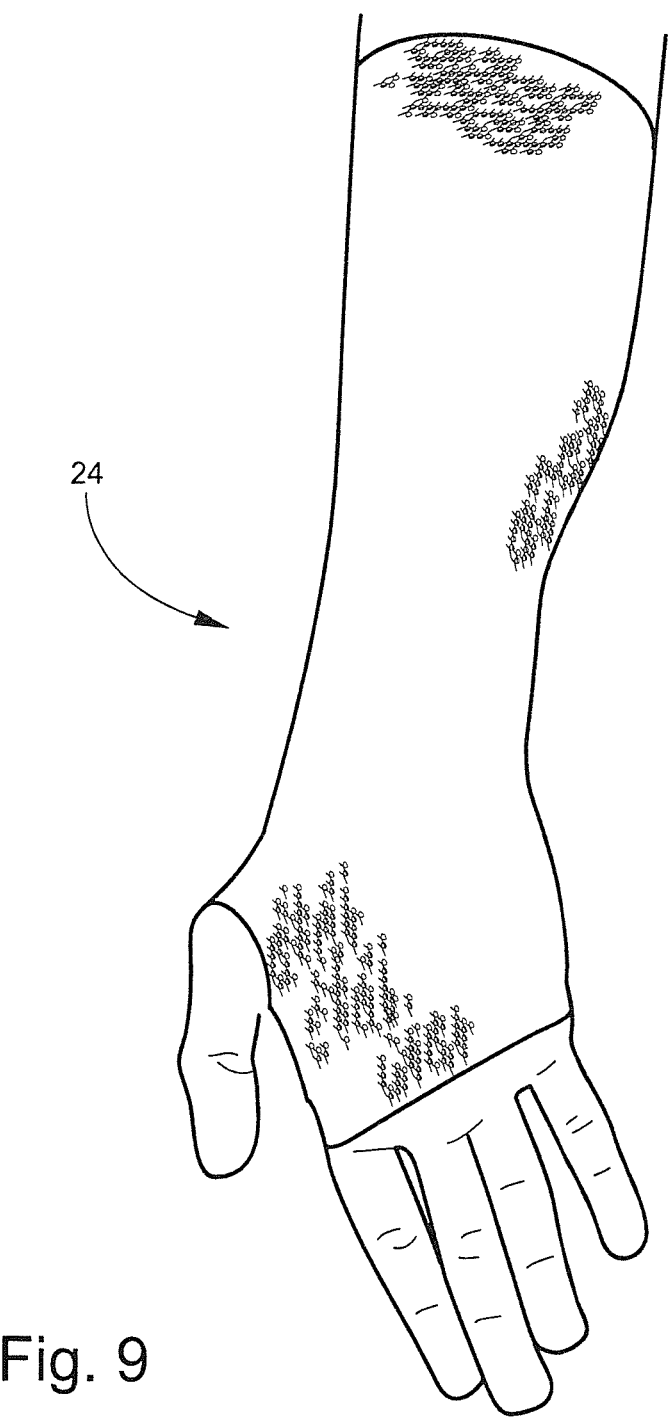
FIG. 9 is a view illustrating application of the tubular stockinet of FIG. 8 to the forearm.
Figure 10:
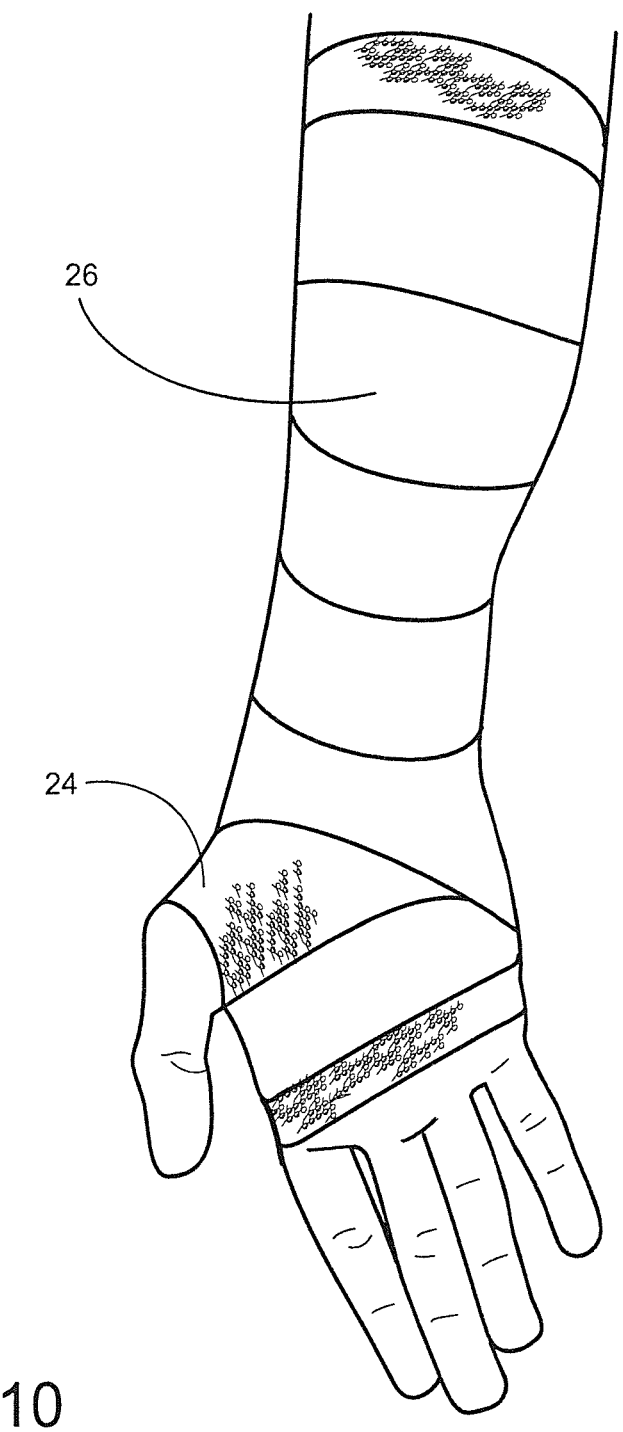
FIG. 10 is a view illustrating application of the fabric in flat form to the wrist and forearm.

Referring to FIG. 8, the fabric may be knitted into a seamless tubular stockinette 24, or "sleeve", having any desired length. Referring to FIG. 9, the tubular stockinette 24 is shown applied to the forearm of a patient. Such a sleeve is useful, for example, in undercast use and in bandaging support wraps particularly for injured human appendages such as legs and arms and even digits such as fingers and toes. Referring to FIG. 10, the fabric may alternatively be knitted into a flat geometry 26 for use as a wrapping around a limb, or for being seamed into a tube.

In one exemplary construction, a stockinette was produced having a diameter of 3 inches, although different diameters are possible. In the 3-inch diameter construction, 10-fold 22 dtex Nylon 66 monofilaments were combined to produce a 220 dtex yarn. Then a knit structure of 1&1 Rib. was produced using a 136 needle-count circular knitting arrangement with a 900 mm dial diameter and 9 courses/cm². The product was then set by annealing following the knitting process at 95 C. for 4 minutes at 40 lbs steam pressure. The annealing process stabilized the knit. For example, 3-inch diameter rolls of 25-meter length were produced.

In another example, yarns having between 10 and 20 filaments were used to make a circularly knitted sleeve according to another embodiment of the invention. Sleeves having 22 dtex are also possible. In yet another embodiment of the invention, the surface area of a 220 dtex yarn formed of 10 small yarns is believed to have such a greater surface area and surface tension that water intrusion is retarded mechanically without a finish being needed. It is believed that below 26 courses per inch and 20 needles per inch the product ladders or frays undesirably.

While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A water resistant medical bandaging product comprising a knitted body consisting of uncoated synthetic yarns, wherein:
   each of the uncoated synthetic yarns is a bundled group of parallel monofilaments including between 10 and 20 monofilaments,
   the knitted body has a mass per unit area from 20 g/m² to less than 90 g/m²,
   the medical bandaging product is an undercast padding that is a knitted, seamless tubular sleeve,
   the medical bandaging product is free of water-resistant chemical finishes, and
   the medical bandaging is free of elastic threads.

2. The water resistant medical bandaging product according to claim 1, wherein the knitted body comprises about 342 openings per square inch when the medical bandaging product is in a relaxed state.

3. The water resistant medical bandaging product according to claim 1, wherein the monofilaments are constructed from Nylon 66.

4. The water resistant medical bandaging product of claim 1, wherein each of the monofilaments has a linear mass density of about 22 decitex.

5. A water resistant medical bandaging product comprising a knitted body consisting of uncoated synthetic yarns, wherein:
   each of the uncoated synthetic yarns is a bundled group of parallel monofilaments including between 10 and 20 monofilaments,
   the knitted body has a mass per unit area from 20 g/m² to less than 90 g/m²,
   the medical bandaging product is free of water-resistant chemical finishes, and
   the medical bandaging is free of elastic threads.

* * * * *